United States Patent [19]

Wagner, Jr. et al.

[11] 4,000,269

[45] Dec. 28, 1976

[54] S-(α-SUBSTITUTED-ARYLMETHYLTHIO, -ARYLMETHYLSULFINYL, AND -ARYLMETHYLSULFONYL)METHYL PHOSPHORUS ESTERS USED AS INSECTICIDES

[75] Inventors: Frank Albert Wagner, Jr.; Roger Williams Addor, both of Pennington, N.J.

[73] Assignee: American Cyanamid Company, Stamford, Conn.

[22] Filed: Aug. 6, 1975

[21] Appl. No.: 602,485

Related U.S. Application Data

[60] Division of Ser. No. 458,376, April 5, 1974, Pat. No. 3,925,516, which is a continuation-in-part of Ser. No. 347,308, April 2, 1973, abandoned.

[52] U.S. Cl. .............................. 424/216; 424/210
[51] Int. Cl.² ........................................... A01N 9/36
[58] Field of Search ............................ 424/216, 210

[56] References Cited

UNITED STATES PATENTS

| | | |
|---|---|---|
| 2,923,730 | 2/1960 | Schrader .................. 260/948 |
| 2,963,505 | 12/1960 | Muhlmann et al. ............. 260/948 |
| 3,171,853 | 3/1965 | Lorenz et al. ................. 260/948 |
| 3,444,274 | 5/1969 | Schrader ................. 260/940 X |
| 3,518,261 | 6/1970 | Nguyen et al. ............ 260/940 X |
| 3,718,718 | 2/1973 | Addor et al. .................... 260/948 |

FOREIGN PATENTS OR APPLICATIONS 2,119,211   12/1971   Germany ....................... 260/948

*Primary Examiner*—Leonard Schenkman
*Attorney, Agent, or Firm*—Harry H. Kline

[57] ABSTRACT

There are provided novel S-(α-substituted -arylmethylthio, -arylmethylsulfinyl, and -arylmethylsulfonyl) methyl phosphorus esters of reduced mammalian toxicity and methods for controlling insects and acarids therewith. There are also provided methods for protecting plants from attack by insects and acarids by applying an insecticidally or acaricidally effective amount of the aforementioned esters to the foliage of said plants or to the soil in which they are grown.

10 Claims, No Drawings

S-(α-SUBSTITUTED-ARYLMETHYLTHIO, -ARYLMETHYLSULFINYL, AND -ARYLMETHYLSULFONYL)METHYL PHOSPHORUS ESTERS USED AS INSECTICIDES

This application is a divisional of our copending application, Ser. No. 458,376, filed on Apr. 5, 1974, now U.S. Pat. No. 3,925,516 which issued on Dec. 9, 1975, which in turn is a continuation-in-part of our application, Ser. No. 347,308, filed on Apr. 2, 1973, now abandoned.

The present invention relates to novel phosphorus esters represented by the structural formula:

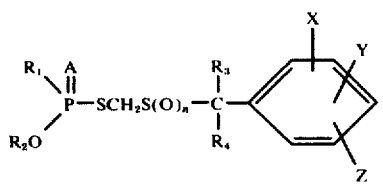

wherein $R_1$ represents a member selected from the group consisting of alkyl from 1 to 4 carbon atoms, alkoxy from 1 to 4 carbon atoms, alkoxyalkyl from 3 to 6 carbon atoms, alkoxy-alkylthio from 3 to 6 carbon atoms, alkylthio from 1 to 4 carbon atoms, phenyl, and $NR_5R_6$; $R_2$ is alkyl from 1 to 4 carbon atoms; $R_3$ represents a member selected from the group consisting of hydrogen, alkyl from 1 to 4 carbon atoms, mono, di and trihaloalkyl $C_1$-$C_4$ and phenyl; $R_4$ is alkyl of from 1 to 4 carbon atoms, and when $R_3$ and $R_4$ are taken together with the central carbon they may form an alicyclic ring of from 3 to 8 carbon atoms; $R_5$ and $R_6$ each represent a member selected from the group consisting of hydrogen and alkyl $C_1$-$C_4$; A represents a member selected from the group consisting of sulfur and oxygen; $n$ represents an integer from 0 to 2; X and Y each represent hydrogen, alkyl from 1 to 4 carbon atoms (straight or branched chain) or halogen; and Z represents a member selected from the group consisting of hydrogen, alkyl from 1 to 4 carbon atoms (straight or branched chain), cyano, halogen, alkoxy $C_1$ to $C_4$, alkylthio from 1 to 4 carbon atoms, $CCl_3$, $CF_3$, carb(lower)alkoxy, nitro and sulfamoyl. The invention is also concerned with a method for controlling insects and acarids with the aforementioned compounds by applying an insecticidally or acaricidally effective amount thereof to the habitat of said pests. Still more particularly, the invention relates to methods for protecting living plants, such as agronomic crops, ornamentals, and the like, by applying a small, but effective, amount of a compound having the aforementioned structures, to the foliage of said plants or to the soil in which they are grown. This invention also contemplates a method for protecting animals from attack by insects and acarids, particularly, fleas and ticks, by topically applying to the host animal an insecticially or acaridally effective amount of a compound of the invention.

In accordance with the process of the invention, the S-(α-substituted-arylmethylthio)methyl phosphorus esters can be prepared by the reaction of an appropriate α-substituted arylmethylthiol with an appropriate S-chloromethyl-substituted phosphorus ester. The reaction is preferably carried out in the presence of an alkali metal alkoxide having one to eight carbon atoms and a saturated alcohol having one to eight carbon atoms. However, the reaction may also be conducted in a solvent, such as dimethylsulfoxide or dimethylformamide, in the presence of a base, such as sodium or potassium hydroxide. Regardless of the solvent system utilized, the reaction can be carried out over a wide temperature range between the freezing and boiling points of the solvent employed, and usually between 0° C. and 100° C. The reaction can be graphically illustrated as follows:

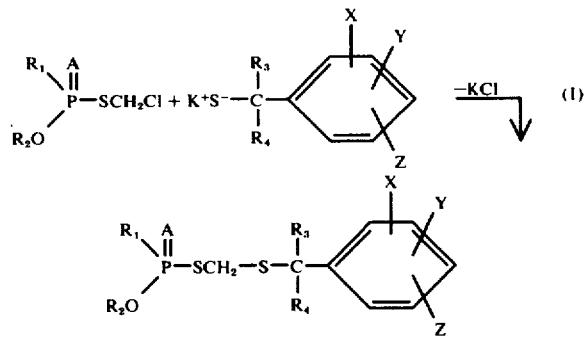

wherein $R_1$, $R_2$, $R_3$, $R_4$, A, X, Y and Z are as defined hereinabove.

In an alternative procedure, the S-(α-substituted-arylmethylthio)methyl phosphorus esters can be prepared by reacting the appropriately substituted phosphorus acid, or the alkali metal or amine salt thereof, with the appropriate chloromethyl thioether. The alkali metal salt reaction may be graphically illustrated as follows, using potassium as the alkali metal:

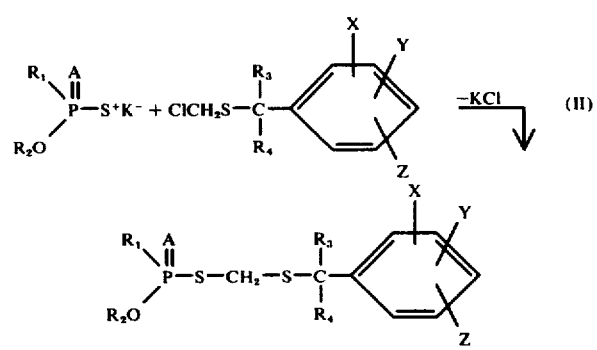

wherein $R_1$, $R_2$, $R_3$, $R_4$, A, X, Y and Z are as defined above.

This reaction is preferably carried out in a solvent, such as a ketone, a chlorinated hydrocarbon, a polyether or an aromatic hydrocarbon. Representative solvents are acetone, ethyl methyl ketone, methylene chloride, dichloroethane, xylene, toluene, benzene, and the like. Mixtures, such as water and an insoluble organic solvent also may be used. This reaction is usually carried out at a temperature between 0° C. and 100° C., or as further limited by the freezing or boiling point of the solvent.

Advantageously, the reaction of the appropriately substituted phosphorus acid and an α-substituted-thiol can also be carried out in the presence of methanol-free formalin at a temperature between about 0° C. and 100° C. This reaction yields the desired ester, as graphically illustrated:

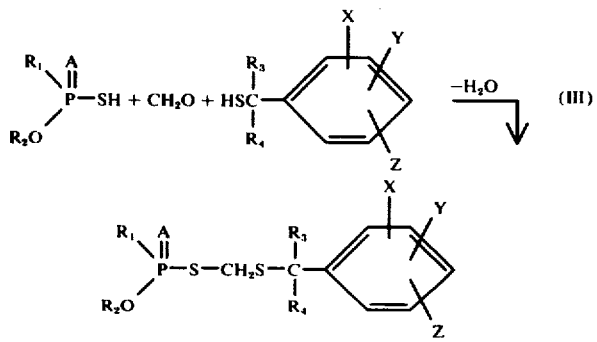

To convert the above-prepared S-(α-substituted-arylmethylthio)methyl phosphorus ester to the corresponding sulfoxide, said ester can be treated with an equivalent amount of m-chloroperbenzoic acid in the presence of a solvent, such as methylene chloride. Mixing of the reactants is preferably conducted at a temperature between about 0° C. and 10° C., followed by warming to temperatures between 20° C. and 40° C.

Conversion of an S-(α-substituted-arymethylthio)methyl phosphorus ester to the corresponding sulfone can readily be achieved either by the reaction of said ester with potassium permanganate in aqueous tert-butyl alcohol employing magnesium sulfate as a buffer, or by reaction with two equivalent of m-chloroperbenzoic acid in a solvent, such as methylene chloride. The formation of the desired sulfoxides and sulfones of the corresponding phosphorus esters also can be achieved through the use of other oxidizing agents well known in the art such as sodium metaperiodate, hydrogen peroxide, phthalic monoperoxy acid, other peracids, and chromic acid.

The compounds of the present invention are highly effective insecticidal and acaricidal agents. They may be applied with conventional type applicators as contact, soil or systemic insecticides and acaricides and may be used in combination with a wide variety of adjuvants and formulation aids. They may be advantageously employed in combination with solid or liquid adjuvants in the form of granular formulations, wettable powders, emulsifiable concentrates, dusts, dust concentrates, and the like. The compounds of this invention also have the advantage that they exhibit extended or enhanced residual insecticidal and acaricidal effectiveness. Further, they can be applied by utilizing ultra low volume techniques as in U.S. Pat. No. 3,515,782.

With conventional type formulations, the active ingredient can be initially formulated as a concentrated composition, comprising a substantial amount of the active ingredient and a minor amount of solid or liquid adjuvant which serves as a formulation aid or conditioning agent, permitting the concentrates to be further mixed with a suitable solid or liquid carrier.

Useful liquid adjuvants in which the toxicant can be dissolved, suspended or distributed include, for example, xylene, benzene, lower aliphatic alcohols, fuel oil, or the like, with or without a dispersant, surfactant and/or emulsifying agent. For application, the concentrate containing about 5% to 95% by weight of the active phosphorus ester is usually diluted with water or a relatively inexpensive organic diluent, such as deodorized kerosene, and applied as a dilute spray containing from about 0.5 ppm. to about 5000 ppm. of the active compound.

Suitable solid adjuvants include, for instance, attapulgite, kaolin, talc, diatomaceous earth, silica, corn cob grits, coconut shell, or the like, in granular or finely ground form. The active ingredient can be conveniently formulated with the solid adjuvants as dusts, dust concentrates, wettable powders, granulars, and the like.

Dusts are generally prepared by mixing or grinding together from about 1% to 10% by weight of the active ingredient with the finely divided solid inert diluent. These formulations can then be applied with dusting equipment to the foliage of agronomic crops or fields, meadows, forests, or the like, which are to be protected from insect attack. In practice, it is generally sufficient to provide between about 0.125 pound and 8 pounds per acre of active material.

Dust concentrates are usually prepared in the same manner as dusts. However, from about 25% to 75% by weight of the active compound, and from 75% to 25% by weight of diluent are generally used.

Wettable powders are prepared in the same fashion as the dust concentrates; however, from about 1% to 5% by weight of an emulsifying or surface active agent, and from about 1% to 5% by weight of a dispersing agent are usually included in such formulations. Polyethylene glycols, methoxy polyethylene glycols, sodium lignosulfonate, calcium dodecylbenzene sulfonat polyoxyethylated vegetable oil, alkyl phenoxy polyoxyethylene ethanol, and the like, are among the surfactants, emulsifying agents and dispersing agents which can be used in these formulations. In practice, the wettable powders are generally dispersed in water and applied as a dilute spray to the vegetation, soil or habitat where insect and/or acarid control is desired.

Insect and acarid control and plant protection in fields, forests, crop lands, and the like, are generally achieved with the compounds of the present invention applied at rates of from about 0.25 pound to about 8 pounds per acre.

Advantageously, the compounds of the present invention exhibit a high order of pesticidal activity and low mammalian toxicity. The increased margin of safety with respect to manufacture, handling and storing obtained with compounds of the present invention is particularly significant, since spray application is feasible with these compounds where such is not true or is significantly more hazardous in the case of closely related prior art compounds.

The invention may be better understood by referring to the examples provided below which are taken as merely illustrative. Unless otherwise specified, the parts are given by weight and the analysis is in percent.

EXAMPLE 1

Preparation of the Intermediate: α,α-Dimethyl α-toluenethiol

To 227 ml. of 48% hydrobromic acid (2.00 mole), cooled to 0° C. to 5° C., is added 76.1 grams (1.00 mole) of thiourea; a considerable amount of the thiourea dissolves. To the stirred slurry is carefully added 136 grams (1.00 mole) of α,α-dimethylbenzyl alcohol, during 2 hours. The reaction mixture temperature is controlled at 25° C. to 30° C. with an ice bath during the addition. After about one-third of the alcohol has been added, the mixture becomes extremely thick; at this point an additional 114 ml. of the concentrated acid is added (total = 341 ml., 3.00 moles) and the alcohol addition is completed. To the thick reaction mixture is added 400 grams of crushed ice, resulting in a strong endotherm, and the mixture is stirred until the ice melts. This mixture, still at <0° C., is filtered on a sintered glass funnel and the filter cake is washed with ether and stored in vacuo over potassium hydroxide overnight. The isothiouronium salt solids weighing 280 grams, apparently still wet, exhibit a melting point range from 84° C. to 94° C. The yield is essentially quantitative.

A solution of 60 grams (1.5 moles) of sodium hydroxide in 1.2 liters of water is next prepared, which results in a solution temperature of 40° C. The above prepared isothiouronium salt is added immediately (no detectable exotherm), and the mixture is stirred overnight. To this rapidly stirred mixture is added 200 ml. of ether, and this mixture is made strongly acidic by the slow addition of 50 ml. of concentrated hydrochloric acid with cooling. The organic layer is collected. The aqueous layer is extracted with two 200 ml. portions of ether. The three organic layers are combined, washed with two 100 ml. portions of saturated sodium chloride solution, and dried over magnesium sulfate. Evaporation of the ether from the dried solution, at 30°C. /12 mm. Hg., gives 128 grams (84.3% based on alcohol) of clear, mobile liquid with a faint yellow cast. Distillation through a simple head gives the pure product α,α-dimethyl α-toluenethiol; boiling point 63°C. to 64°C/2.3 mm. Hg.

EXAMPLE 2

Preparation of S-(α,α-Dimethylbenzylthio)methyl O,O-DiethylPhosphorodithicate

To 15.2 grams (0.100 mole) of α,α-dimethyl-α-toluenethiol in 50 ml. of tert-burtyl alcohol is added 11.2 grams (0.100 mole) of potassium tert-butoxide. The solution is cooled to room temperature and is added slowly to a solution of 23.5 grams (0.100 mole) of S-chloromethyl O,O-diethyl phosphorodithioate in 50 ml. of tert-butyl alcohol. A slow, mild exotherm ensues. The temperature of the reaction mixture is maintained at 25°C. to 30°C. with a water bath. The reaction mixture is stirred at room temperature for 20 hours, and then the solvent is removed at 35°C. and 12 mm. Hg. The residue is partitioned between 150 ml. of methylene chloride and 75 ml. of 1.7% potassium hydroxide solution. The organic phase is washed with a solution prepared from 25 ml. of 5% potassium hydroxide plus 25 ml. of saturated sodium chloride solution then with three 25 ml. portions of saturated sodium chloride, two 25 ml. portions of 5% hydrochloric acid, three 25 ml. portions of saturated sodium chloride, 25 ml. of 5% potassium hydroxide, and three 25 ml. portions of saturated sodium chloride. The organic phase is dried with magnesium sulfate, and the solvent removed, ultimately at 60°C./0.5 mm. Hg., to give 30.9 grams (88.3%) of moderately viscous, clear, straw-colored liquid. This material is dissolved in carbon tetrachloride and placed on a 2 ¼ inch i.d. column containing 20 inches of 60 to 100 mesh Florisil magnesium silicate. The column is eluted with 1.5 liters of carbon tetrachloride, then successively with 1 liter portions of 5, 10, 15, 20 and 25 volume percent methylene chloride in carbon tetrachloride, and finally with one liter of methylene chloride. The residue obtained from the removal of the solvents from the last three effluent fractions is a clear, faintly straw-colored, moderately viscous liquid with $n_D^{23.6}$=1.5706, a theoretical proton magnetic resonance integral, and the following analysis.

Analysis. Calculated for $C_{14}H_{23}O_2PS_3$: C, 47.98; H, 6.61; S, 27.44. Found: C, 48.19 and 48.24; H, 6.57 and 6.63; S, 27.73 and 27.71.

The solvents are evaporated from the three effluent fractions preceding those worked up above, and from a 1.5 liter methylene chloride fraction, following those worked up above, to give additional material which appears to be of quality equivalent with that obtained above, by thin-layer chromatographic analysis. Total yield = 13.9 (40%).

EXAMPLE 3

Preparation of S-(α,α-Dimethylbenzylthio)methyl O,O-Diethyl Phosphorodithioate

To a solution of 43.7 grams (0.234 mole) of o,o-diethyl phosphordithioic acid and 47.0 grams (0.234 mole) of chloromethyl α,α-dimethylbenzyl sulfide (which is prepared, for example, by the reaction of the thiol, paraformaldehyde and gaseous hydrogen chloride in methylene chloride at low temperature) in 200 ml. of methylene chloride is added, dropwise, a solution of 23.7 grams (23.7 ml., 0.234 mole) of triethylamine in 50 ml. of methylene chloride. The addition is carried out during 20 minutes, and the reaction mixture temperature is maintained at 20°C. to 25°C. with an ice bath. The mixture is stirred at room temperature for 2.5 hours (an extremely mild, slow exotherm is noted during the early part of this period) and is then heated at reflux for 30 minutes. The cooled reaction mixture is washed with 50 ml. of water, 25 ml. of 5% hydrochloric acid, 25 ml. of saturated sodium chloride solution, 25 ml. of 5% potassium hydroxide solution, and two 25 ml. portions of saturated sodium chloride. The solvent is removed from the dried (magnesium sulfate) solution to give 76.0 grams (92.7%) of pale yellow liquid. Comparison of the proton magnetic resonance spectrum of this material with that of the analytical sample, above, shows this present sample to be approximately 95 wt. percent the desired product.

EXAMPLE 4

Preparation of S-($\alpha,\alpha$-Dimethylbenzylthio)methyl O,O-Diethyl Phosphorodithioate A mixture of 37.2 grams (0.200 mole) of O,O-diethyl phosphorodithioic acid, 30.5 grams (0.200 mole) of $\alpha,\alpha$-dimethyl $\alpha$-toluenethiol and 16.5 ml. (0.220 mole) of methanol-free formalin is stirred vigorously at room temperature for 3 days. The mixture is extracted with 250 ml. of methylene chloride, and this solution is washed with two 30 ml. portions of saturated sodium chloride solution, four 30 ml. portions of 5% potassium hydroxide solution, and three 30 ml. portions of saturated sodium chloride. Evaporation of the solvent from the dried (magnesium sulfate) solution gives a colorless, moderately viscous liquid residue. The proton magnetic resonance spectrum of this material establishes that the desired product is the major component.

EXAMPLE 5

Preparation of S-($\alpha,\alpha$-Dimethylbenzylthio)methyl O,O-Dimethyl Phosphorodithioate To 0.078 mole of chloromethyl $\alpha,\alpha$-dimethylbenzyl sulfide in 100 ml. of acetone is added 15.3 grams (0.078 mole) of sodium O,O-dimethyl phosphorodithioate followed by stirring overnight. The reaction mixture is maintained at a temperature of 25° C. to 30° C.

The acetone is evaporated, the residue is suspended in 200 ml. of methylene chloride, and the organic solution washed with water and 5% sodium hydroxide solution. The organic solution is dried with magnesium sulfate. Evaporation of the solvent gives 25.0 grams (99%) of a colorless liquid. This material is chromatographically purified on a silica gel dry-column using 25 volume percent methylene chloride in hexane as the eluant. 9.2 grams of colorless liquid is obtained, with proton magnetic resonance and infrared spectra confirming the assigned structure.

Analysis. Calculated for $C_{12}H_{19}O_2PS_3$: C, 44.72; H, 5.90. Found: C, 44.54; H, 6.00.

EXAMPLE 6

Preparation of S-(p-Chloro-$\alpha,\alpha$-Dimethylbenzylthio)methyl O,O-Diethyl Phosphorodithioate To 32.5 g. of chloromethyl p-chloro-$\alpha,\alpha$-dimethylbenzyl sulfide (prepared for p-chloro-$\alpha,\alpha$-dimethyl $\alpha$-toluenethiol obtained as in Example 1 from p-chloro-$\alpha,\alpha$-dimethylbenzyl alcohol) in 250 ml. of acetone is added 23.4 g. of potassium O,O-diethyl phosphorodithioate. After stirring the mixture for several hours at room temperature the bulk of the acetone is removed under vacuum and the residue is mixed with methylene chloride. The methylene chloride mixture is washed with water and then dried over magnesium sulfate. Removal of solvent under vacuum leaves 38.2 g. of crude product which is purified by the dry-column technique on a 1.5 inch diameter column of silica gel using 25% methylene chloride in hexane as the developing solvent and ultraviolet light for detection. A major band, cut from the column and eluted with ethyl acetate, affords 12.8 g. colorless product on concentration. It is homogeneous by thin layer chromatography and the structure is consistent with both the infrared and proton magnetic resonance spectra.

Analysis. Calculated for $C_{14}H_{22}ClO_3PS$; C, 43.70; H, 5.72. Found: C, 42.59; H, 5.72.

EXAMPLE 7

Preparation of S-(p-Chloro-$\alpha,\alpha$-dimethylbenzylthio)methyl O,O-Dimethyl Phosphorodithioate Following the procedure of Example 6, but substituting potassium O,O-dimethyl phosphorodithioate for potassium O,O-diethyl phosphorodithioate, gives the purified product as a colorless oil.

Analysis. Calculated for $C_{12}H_{18}ClO_2PS_3$: C, 40.40; H, 5.05. Found: C, 40.13; H, 5.12.

EXAMPLE 8

Preparation of S-(3,4-Dichloro-$\alpha,\alpha$-dimethylbenzylthio)methyl O,O-Diethyl Phophorodithioate Using 3,4-dichloro-$\alpha,\alpha$-dimethyl-$\alpha$-toluenethiol prepared from 3,4dichloro-$\alpha,\alpha$-dimethylbenzyl alcohol by the procedure of Example 1 and following the procedure of Example 6, the desired product is obtained as a colorless oil.

Analaysis. Calculated for $C_{14}H_{21}Cl_2O_2PS_3$: C, 40.11; H, 5.01; Cl, 16.92; P, 7.39; S, 22.94. Found: C, 39,97; H, 5.07; Cl, 17.06; P, 7.30; S, 23.04.

EXAMPLE 9

Preparation of S-($\alpha,\alpha$-Dimethyl-2,4,5-trichlorobenzylthio)- methyl O,O-Diethyl Phosphorodithioate Using $\alpha,\alpha$-dimethyl-2,4,5-trichloro-$\alpha$-tolunenethiol prepared from $\alpha,\alpha$-dimethyl-2,4,5-trichlorobenzyl alcohol by the procedure of Example 1, and following the procedure of Example 6, desired product is obtained as a colorless oil.

Analysis. Calculated for $C_{13}H_{20}Cl_3O_2PS_3$: C, 37.06; H, 4.41. Found: C, 38.40 and 38.23; H, 4.33 and 4.33.

EXAMPLE 10

Preparation of S-(2,5-Dichloro-$\alpha,\alpha$-dimethylbenzylthio)-methyl O,O-Diethyl Phosphorodithioate Using 2,5-dichloro-$\alpha,\alpha$-dimethyl-$\alpha$-toluenthiol prepared from 2,5-dichloro-$\alpha,\alpha$-dimethylbenzyl alcohol by the procedure of Example 1 and following the procedure of Example 6, the desired product is obtained as a colorless oil.

Analysis. Calculated for $C_{14}H_{21}Cl_2O_2PS_3$: C, 40.11; H, 5.01. Found: C, 40.62; H, 5.00.

EXAMPLE 11

Preparation of S-(3,4-Dichloro-$\alpha,\alpha$-dimethylbenzylthio)methyl O,O-Dimethyl Phosphorodithioate Using 3,4-dichloro-$\alpha,\alpha$-dimethyl-$\alpha$-toluenethiol prepared from 3,4-dichloro-$\alpha,\alpha$-dimethylbenzyl alcohol by the procedure of Example 1, and using potassium O,O-dimethyl phosphorodithioate in place of potassium O,O-diethyl phosphorodithioate, the procedure of Example 6 gives the desired product as a colorless oil.

Analysis. Calculated for $C_{12}H_{17}Cl_2O_2PS_3$: C, 36.84; H, 4.35. Found: C, 36.83; H, 4.34.

EXAMPLE 12

Preparation of S-($\alpha,\alpha$-Dimethylbenzylthio)methyl O-Ethyl S-Propyl Phosphorodithioate Proceeding in the same manner as Example 5, and substituting sodium O-ethyl S-propyl phosphorodithioate for O,O-dimethyl phosphorodithioate, gives the expected product as an oil.

Analysis. Calculated for $C_{15}H_{25}PO_2S_3$: C, 49.45; H, 6.86. Found: C, 49.23; H, 6.84.

EXAMPLE 13

Preparation of S-(p-Bromo-$\alpha,\alpha$-dimethylbenzylthio)methyl O,O-Dimethyl Phosphordithioate Using p-bromo-$\alpha,\alpha$-dimethyl-$\alpha$-toluenethiol prepared from p-bromo-$\alpha,\alpha$-dimethylbenzyl alcohol by the procedure of Example 1, and using potassium O,O-dimethyl phosphorodithioate in place of potassium O,O-diethyl phosphorodithioate, the procedure of Example 6 gives the desired product as a colorless oil.

Analysis. Calculated for $C_{12}H_{18}BrPO_2S_3$: C, 35.92: H, 4.49. Found: C, 35.95; H, 4.63.

EXAMPLE 14

Preparation of S-(m,$\alpha,\alpha$-Trimethylbenzylthio)methyl O,O-Diethyl Phosphorodithioate Using m, $\alpha,\alpha$-trimethyl-$\alpha$-toluenethiol prepared from m,$\alpha,\alpha$-trimethylbenzyl alcohol by the procedure of Example 1 and following the procedure of Example 6, the desired product is obtained as a colorless oil.

Analysis. Calculated for $C_{12}H_{25}O_2PS_3$: C, 49.45; H, 6.86. Found: C, 49.54; H, 6.85.

EXAMPLE 15

Preparation of S-($\alpha$-Methylbenzylthio)methyl O,O-Diethyl Phosphorodithioate Following the same procedure as in Example 4, but substituting $\alpha$-methyl-$\alpha$-toluenethiol for $\alpha,\alpha$-dimethyl-$\alpha$-toluenethiol, and effecting purification with column chromatography, there is obtained the desired product as a colorless oil.

Analysis. Calculated: C, 46.43; H, 6.24. Found: C, 46.42; H, 6.05.

EXAMPLE 16

Preparation of S-(p-Chloro-$\alpha,\alpha$-dimethylbenzylthio)methyl O-Methyl S-Methyl Phosphorodithioate Following the procedure of Example 6 but substituting potassium O-methyl S-methyl phosphorodithioate for potassium O,O-diethyl phosphorodithioate gives the purified product as a colorless oil.

Analysis. Calculated for $C_{12}H_{18}ClO_2PS_3$: C, 40.40; H, 5.05. Found: C, 41.18; H, 5.17.

EXAMPLE 17

Preparation of S($\alpha,\alpha$-Dimethylbenzylthio)methyl O-Methyl Phosphoramidothioate Following the procedure of Example 5, potassium O-methyl phosphoramidothioate gives the desired product.

EXAMPLE 18

Preparation of S-($\alpha,\alpha$-Dimethylbenzylthio)methyl O-Methyl S-2-Methoxyethyl Phosphorodithioate Following the procedure of Example 5, potassium S-2-methoxyethyl O-methyl phosphorodithioate gives the desired product. Compounds of this type also are obtained by demethylation of the O,O-dimethyl ester of S-($\alpha,\alpha$-dimethylbenzylthio)methyl phosphorodithioic acid (Example 5) by known methods (for example, with hydrosulfide ion, tertiary amine bases, O,O-diisopropyl phosphorodithioate ion, iodide ion), and realkylation of the intermediate O-methyl S-($\alpha,\alpha$-dimethylbenzylthio)methyl phosphorodithioate with an appropriate alkyl or substituted alkyl halide.

EXAMPLE 19

Preparation of S-($\alpha,\alpha$-Dimethylbenzylthio)methyl O-Isopropyl O-Methyl Phosphordithioate Following the procedure of Example 5, potassium O-methyl O-isopropyl phosphorodithioate gives the desired product. Alternatively, this compound is obtained by hydrolysis of the O,O-diethyl ester of S-($\alpha,\alpha$-dimethylbenzylthio)methyl phosphorodithioic acid of Example 2 (for example, with an aqueous alkali metal hydroxide) and subsequent reaction of the formed ($\alpha,\alpha$-dimethylbenzylthio)methanethiol with O-methyl O-isopropyl phosphorochloridothioate, in the presence of, for example, alkali metal alkoxides or tertiary amines.

EXAMPLE 20

Preparation of S-($\alpha,\alpha$-Dimethylbenzylthio)methyl O,O-diisopropyl Phosphorodithioate Following the procedure of Example 5, in every detail except that potassium O,O-diisopropyl phosphorodithioate is substituted for the O,O-dimethyl phosphorodithioate reactant, gives the desired product.

Analysis. Calculated: C, 50.79; H, 7.14. Found: C, 50.47; H, 7.18.

EXAMPLE 21

Preparation of S-($\alpha$-Ethyl-$\alpha$-methylbenzylthio)methyl O,O-Diethyl Phosphorodithioate To 0.091 mole of chloromethyl $\alpha$-ethyl-$\alpha$-methylbenzyl sulfide and 16.9 grams (0.091 mole) of the phosphorodithioate of the formula $(C_2H_5O)_2PSSH$ in 100 ml. of ether is added 9.2 grams of triethylamine, dropwise, maintaining the temperature at 25° C. The mixture is stirred for several hours and then washed with water and 5% sodium hydroxide solution. Evaporation of the solvent from the dried (magnesium sulfate) solution gives 31.3 grams (95%) of a colorless liqiuid. This material is chromatographically purified on a silica gel dry-column using 10 volume percent methylene chloride in hexane as the eluant.

6.3 Grams of liquid is obtained with proton magnetic resonance and infrared spectra indicating analytical purity.

Analysis. Calculated for $C_{15}H_{25}O_2PS_3$: C, 49.45; H, 6.86. Found: C, 49.32; H, 6.91.

An additional 6.0 grams of liquid of estimated 85% to 90% purity also is obtained.

EXAMPLE 22

Preparation of S-(α,α-Diethylbenzylthio)methyl O,O-Diethyl Phosphorodithioate

In similar manner but substituting chloromethyl α,α-diethylbenzyl sulfide for the chloromethyl α-ethyl-α-methylbenzyl sulfide, there is obtained the desired product.

Analysis. Calculated: C, 50.79; H, 7.14. Found: C, 50.81; H, 7.31.

EXAMPLE 23

Preparation of S-(2,3-Dichloro-α,α-dimethylbenzylthio)methyl O,O-Dimethyl Phosphorodithioate Using chloromethyl 2,3-dichloro-α,α-dimethylbenzyl sulfide (prepared from 2,3-dichloro-α,α-dimethyl-α-toluenethiol obtained as in Example 1 from 2,3-dichloro-α,α-dimethylbenzyl alcohol) and stirring vigorously for 2 hours at 50° C. with a 10% excess of 50% aqueous sodium O,O-dimethyl phosphorodithioate solution gives a crude product which is purified as in Example 6 to give the pure, desired product as a colorless oil.

Analysis. Calculated for $C_{12}H_{17}Cl_2O_2PS_3$: C, 36.84; H, 4.35. Found: C, 37.85 and 37.72; H, 4.45 and 4.45.

EXAMPLE 24

Preparation of S-(p-Cyano-α,α-dimethylbenzylthio)methyl O,O-Dimethyl Phosphorodithioate Following the procedure of the above Example, using chloromethyl p-cyano-α,α-dimethylbenzyl sulfide, gives the purified product as a colorless oil.

Analysis. Calculated for $C_{13}H_{18}NO_2PS_3$: C, 44.96; H, 5.18; N, 4.03. Found: C, 44.57; H, 5.39; N, 3.82.

EXAMPLE 25

Preparation of S-(2,5-Dichloro-α,α-dimethylbenzylthio)methyl O,O-dimethyl Phosphorodithioate In similar manner, using chloromethyl 2,5-dichloro-α,α-dimethylbenzyl sulfide, the purified product is obtained as a colorless oil.

Analysis. Calculated for $C_{12}H_{17}Cl_2O_2PS_3$: C, 36.84; H, 4.35. Found: C, 38.64; H, 4.42.

EXAMPLE 26

Preparation of S-(p-Methylthio-α,α-dimethylbenzylthio)-methyl O,O-Dimethyl Phosphorodithioate In similar manner, using chloromethyl p-methylthio-α,α-dimethylbenzyl sulfide, the purified product is obtained as a colorless oil.

Analysis. Calculated for $C_{13}H_{21}O_2PS_4$: C, 42.39; H, 5.70. Found: C, 42.66; H, 5.71.

EXAMPLE 27

Preparation of S-(α,α-Dimethylbenzylsulfinyl)methyl O,O-Diethyl Phosphorodithioate A solution of 20 grams (0.057 mole) of the phosphorodithioate product of Example 2 in 100 ml. of methylene chloride is cooled to 5° C. to 10° C., and 11.6 grams of 85% m-chloroperbenzoic acid is added protion-wise during 15 to 20 minutes. The reaction mixture temperature is maintained at 10° C. during the addition.

The heterogenous mixture is stirred overnight at room temperature, and then filtered. The filtrate is washed with sodium carbonate solution and dried with magnesium sulfate. Evaporation of the solvent gives 20.9 grams of a pale yellow liquid (100% yield). This material is chromatographically purified on a silica gel dry-column, using methylene chloride as the eluant.

7.5 Grams of a colorless liquid is obtained, with proton magnetic resonance and infrared spectra substantiating the assigned structure.

Analysis. Calculated for $C_{14}H_{23}O_3PS_3$: C, 45.90: H, 6.28. Found: C, 44.67; H, 6.06.

EXAMPLE 28

Preparation of S-(α,α-Dimethylbenzylsulfinyl)methyl O,O-Diisopropyl Phosphorodithioate The procedure of the above example is employed except that O,O-diisopropyl S-(α,α-dimethylbenzylthio)methyl phosphorodithioate is substituted for the O,O-diethyl S-(α,α-dimethylbenzylthio)methyl phosphorodithioate, and gives the desired product.

Analysis. Calculated: C, 48.73; H, 6.85. Found: C, 48.87; H, 6.85.

EXAMPLE 29

Preparation of S-(α,α-Dimethylbenzylsulfonyl)methyl 0,0-Diethyl Phosphorothioate To a solution of 0,0-diethyl S-(α,α-dimethylbenzylthio)methyl phosphorothioate (0.050 mole) in 100 ml. of methylene chloride, cooled to 0° C. to 5° C., is added the solid m-chloroperoxybenzoic acid (20.4 grams of assumed 85% purity, 17.3 grams real, 0.10 mole) during 1 hour; the temperature of the exothermic reaction is maintained at 5° C. to 10° C. during the addition with external cooling. The reaction mixture is stirred for several minutes at ca. 5° C., allowed to warm, and then stirred at room temperature overnight. The mixture is filtered and the filtrate is washed with 50 ml. of 2N sodium hydroxide, 25 ml. of 2N sodium hydroxide, two 25 ml. portions of saturated sodium chloride and dried (magnesium sulfate). Reduced-pressure evaporation of the solvent from the dried solution gives a moderately viscous liquid.

EXAMPLE 30

In a manner similar to that used in Example 3, the following sulfides are substituted for chloromethyl α,α-dimethylbenzyl sulfide to yield the products hereinbelow:

| Sulfide | Product |
|---|---|
| Chloromethyl p-chloro-m,α,α-trimethylbenzyl sulfide | Phosphorodithioic acid, S-(p-chloro-m,α,α-trimethylbenzylthio)methyl O,O-diethyl ester |
| Chloromethyl p-cyano-α,α-dimethylbenzyl sulfide | Phosphorodithioic acid, S-(p-cyano-α,α-dimethylbenzylthio)methyl O,O-diethyl ester |

EXAMPLE 31

In a manner similar to that used in Example 5, the following sulfides are substituted for chloromethyl α,α-dimethylbenzyl sulfide to yield the products hereinbelow:

| Sulfide | Product |
|---|---|
| Chloromethyl α,α-dimethyl-p-nitrobenzyl sulfide | Phosphorodithioic acid, S-(α,α-dimethyl-p-nitrobenzyl-thio)methyl O,O-dimethyl ester |
| Substituted for p-nitro | Substitute for p-nitro |
| 1. -p-trifluoromethyl- | -p-trifluoromethyl- |
| 2. -m-fluoro- | -m-fluoro |
| 3. -p-isopropyl- | -p-isopropyl |
| 4. -m-carbethoxy- | -m-carbethoxy |
| 5. -p-trichloromethyl- | -p-trichloromethyl- |

EXAMPLE 32

Preparation of
S-(α,α-Dimethylbenzylthio)methyl-N,N,O-trimethyl-phosphoramidodithioate Following the procedure of Example 5, but replacing sodium O,O-dimethyl phosphorodithioate with potassium N,N,O-trimethyl phosphoramidothioate affords the subject compound.

dust in 1-ounce jars, and the acetone allowed to evaporate. Twenty-five milliliters of moist soil and about three wheat seeds are placed in the jar, capped, and the contents thoroughly mixed. Ten False wireworm larvae (*Eleodes suturalis*), 10 days old, are then placed in each jar. Mortality counts are made after 6 days and percent mortality determined. Data obtained are provided in Table I below.

Southern Corn Rootworm Control

Compounds are prepared as dusts on talc. The compounds are dissolved in acetone, and appropriate rates obtained by serial dilution. One and one-quarter milliliters of solution is pipetted onto a standard volume of dust in 1-ounce jars, and the acetone allowed to evaporate. Twenty-five milliliters of moist soil and about 200 millet seeds are placed in the jar, capped and the contents thoroughly mixed. Ten second-instar larvae of the Southern corn rootworm (*Diabrotica undecimpunctata*) are then placed in each jar. Mortality counts are made after 6 days and percent mortality determined. Data obtained are provide in Table I below.

TABLE I

Compound $$\begin{array}{c} R_1 \quad A \\ \diagdown \parallel \\ P-SCH_2S(O)_n-C- \\ \diagup \quad | \\ R_2O \quad R_4 \end{array} \bigg\langle \!\!\!\! \bigotimes_{Z}^{X} \!\!\!\! \bigg\rangle$$

| | | | | | | | | | Rate of Application lbs./Acre | | |
|---|---|---|---|---|---|---|---|---|---|---|---|
| | | | | | | | | | | Potting Soil | |
| $R_1$ | $R_2$ | n | $R_3$ | $R_4$ | A | X | Y | Z | 50 | 10 | 1 |
| Percent Control of False Wireworms | | | | | | | | | | | |
| $C_2H_5O$ | $C_2H_5$ | 0 | H | $CH_3$ | S | H | H | H | 100 | 100 | 0 |
| $C_2H_5O$ | $C_2H_5$ | 1 | $CH_3$ | $CH_3$ | S | H | H | H | 100 | 100 | 0 |
| $CH_3O$ | $CH_3$ | 0 | $CH_3$ | $CH_3$ | S | H | H | H | 100 | 100 | 100 |
| $(CH_3)_2CHO$ | $(CH_3)_2CH$ | 0 | $CH_3$ | $CH_3$ | S | H | H | H | 100 | 0 | — |
| $C_2H_5O$ | $C_2H_5$ | 0 | $CH_3$ | $CH_3$ | S | H | H | H | 100 | 100 | 0 |
| Percent Control of Southern Corn Rootworm Larvae | | | | | | | | | | | |
| $C_2H_5O$ | $C_2H_5$ | 0 | H | $CH_3$ | S | H | H | H | 100 | 100 | 80 |
| $C_2H_5O$ | $C_2H_5$ | 1 | $CH_3$ | $CH_3$ | S | H | H | H | 100 | 100 | 0 |
| $CH_3O$ | $CH_3$ | 0 | $CH_3$ | $CH_3$ | S | H | H | H | 100 | 100 | 100 |
| $(CH_3)_2CHO$ | $(CH_3)_2CH$ | 0 | $CH_3$ | $CH_3$ | S | H | H | H | 100 | 0 | — |
| $C_2H_5O$ | $C_2H_5$ | 0 | $CH_3$ | $CH_3$ | S | H | H | H | 100 | 100 | 90 |
| $C_2H_5O$ | $C_2H_5$ | 0 | $CH_3$ | $C_2H_5$ | S | H | H | H | 100 | 100 | 0 |
| $C_2H_5O$ | $C_2H_5$ | 0 | $C_2H_5$ | $C_2H_5$ | S | H | H | H | 100 | 100 | 50 |
| n-$C_3H_7S$ | $C_2H_5$ | 0 | $CH_3$ | $CH_3$ | O | H | H | H | 100 | 100 | 0 |
| $C_2H_5O$ | $C_2H_5$ | 0 | $CH_3$ | $CH_3$ | S | H | 4Cl | H | 100 | 90 | 0 |
| $C_2H_5O$ | $C_2H_5$ | 0 | $CH_3$ | $CH_3$ | S | H | $3CH_3$ | H | 100 | 100 | 100 |
| $CH_3O$ | $CH_3$ | 0 | $CH_3$ | $CH_3$ | S | 3Cl | 4Cl | H | 100 | 100 | 100 |
| $CH_3O$ | $CH_3$ | 0 | $CH_3$ | $CH_3$ | S | H | 4Cl | H | 100 | 100 | 100 |
| $CH_3S$ | $CH_3$ | 0 | $CH_3$ | $CH_3$ | O | H | 4Cl | H | 100 | 100 | 0 |
| $CH_3O$ | $CH_3$ | 0 | $CH_3$ | $CH_3$ | S | H | 4Br | H | 100 | 100 | 90 |
| $CH_3O$ | $CH_3$ | 0 | $CH_3$ | $CH_3$ | S | H | 4CN | H | 100 | 100 | 0 |
| $CH_3O$ | $CH_3$ | 0 | $CH_3$ | $CH_3$ | S | H | 2Cl | 5Cl | 100 | 100 | 0 |
| $C_2H_5O$ | $C_2H_5$ | 0 | $CH_3$ | $CH_3$ | S | 2Cl | 5Cl | H | 100 | 100 | 0 |
| $CH_3O$ | $CH_3$ | 0 | $CH_3$ | $CH_3$ | S | 2Cl | H | 3Cl | 100 | 90 | 60 |

EXAMPLE 33

Preparation of
S-(3,4-Dichloro-α,α-dimethylbenzylthio)methyl-O-ethyl Phenylphosphonodithioate By the reaction of chloromethyl 3,4-dichloro-α,α-dimethylbenzyl sulfide with sodium O-ethyl phenylphosphonodithioate the subject compound is prepared.

EXAMPLE 34

Insecticidal Evaluation (False Wireworm Control)

Compounds are prepared as dusts on talc. The compounds are dissolved in acetone, and appropriate rates obtained by serial dilution. One and one-quarter milliliters of solution is pipetted onto a standard volume of

EXAMPLE 35

Control of Insects and Acarids

The efficacy of the compounds of the present invention for controlling insects and acarids is demonstrated in the following tests. Procedures employed in these tests are provided below as Procedures A through H, and data obtained are reported in Table II.

A. Tarnished Plant Bug — Lygus lineolaris (Palisot de Beauvois)

Test compounds are prepared as 1000 ppm. solutions in 10% acetone, 0.2% Alrodyne 315, and 89.8% water. A tenfold dilution is made with 65% acetone and 35% water. The primary leaves of Sieva lima bean plants are dipped for 3 to 5 seconds in the test solutions and placed in an exhaust hood to dry. When dry, each leaf is placed in a 4-inch petri dish with a moist filter paper on the bottom. Ten adult Lygus bugs are aspirated from the stock culture and placed in the petri dish. The dishes are covered and held at 80° F. and 50% R.H. After 2 days, mortality counts are made.

B. Boll Weevil — *Anthonomus grandis* (Boheman)

Test compounds are prepared as 1000 ppm. solutions in 10% acetone, 0.2% Alrodyne 315, and 89.8% water. A tenfold dilution is made with 65% acetone and 35% water. The first or second true leaf of young cotton plants is dipped for 3 to 5 seconds in the test solution and placed in an exhaust hood to dry. When dry, each leaf is placed in a 4-inch petri dish with a moist filter paper on the bottom. Ten adult boll weevils are removed from the stock culture and placed in the petri dish. The dishes are covered and held at 80° F. and 50% R.H. After 2 days, mortality counts are made.

C. Bean Aphid — *Aphis fabae* (Scopoli)

Compounds are tested at 100, 10 and 1 ppm. in solution or suspension in 65% acetone/35% water. Two-inch fiber pots each containing a nasturtium plant 2 inches high and infested with about 150 aphids 2 days earlier, are placed on a turntable (4 RPM) and sprayed for two revolutions with a No. 154 DeVilbiss Atomizer at 20 psi. air pressure. The spray tip is held about 6 inches from the plants, and the spray is directed so as to give complete coverage of the aphids and the plants. The sprayed plants are laid on their sides on white enamel trays. Mortality estimates are made after holding for 2 days at 70° F. and 50% R.H.

D. Southern Armyworm –*Prodenia eridania* (Cramer)

Compounds are tested at 1000 and 100 ppm. in solution or suspension in 65% acetone/35% water. Sieva lima bean primary leaves are dipped for 3 seconds in the test solution and set in a hood on a screen to dry. When dry, each leaf is placed in a 4-inch petri dish which has a moist filter paper in the bottom and ten third-instar armyworm larvae about ⅜ inch long. The dishes are covered and held at 80° F., and 60% R.H. After 2 days, mortality counts and estimates of the amount of feeding are made. Compounds showing partial kill and/or inhibition of feeding are held an extra day for further observations.

E. Two-spotted Spider Mite — *Tetranychus urticae* (Koch)

Sieva lima bean plants with primary leaves 3 to 4 inches long are infested with about 100 adult mites per leaf 4 hours before use in this test. The mite and egg infested plants are dipped for 3 seconds in the same solutions used in the aphid test, and the plants set in the hood to dry. They are held for 2 days at 80° F., 60% R.H., and the adult mite mortality estimated on one leaf under a steroscopic microscope. The other leaf is left on the plant an additional 5 days and then examined at 10X power to estimate the kill of eggs and of newly hatched nymphs, giving a measure of ovicidal and residual action, respectively.

F. Mexican Bean Beetle — *Epilachna varivestis* (Muls.)

Compounds to be tested are made up as 100 or 10 ppm. solutions in 65% acetone/35% water. Sieva lima bean leaves are dipped in the test solution and set in the hood to dry. When dry, they are placed in 4-inch petri dishes which have a moist filter paper in the bottom, and 10 third-instar bean beetles are added to each dish. The dishes are covered and held at 80° F., 60% R.H. After 2 days, mortality counts and estimates of the amount of feeding are made. Compounds showing kills greater than 75% are further tested at tenfold dilutions in 65% acetone/35% water.

G. Western Potato Leafhopper — *Empoasca abrupta* (Say)

Sieva lima bean plants with the primary leaf expanded to 3 to 4 inches are dipped into 100 or 10 ppm. 50% acetone/50% water solutions and set in the hood to dry. A 1-inch piece of the tip of a treated leaf is cut off and placed in a 4-inch petri dish with a moist filter paper in the bottom. From 3 to 10 second-instar nymphs are tapped from the culture plants into the test dish and rapidly covered. Mortality counts are made after 2 days at 80° F., and 50% R.H.

H. Malaria Mosquito—*Anopheles quadrimaculatus* (Say) Audlt Test

Solutions of 65% acetone/35% water containing 10 ppm. of test compound are poured into wide-mouth 2-ounce jars, each containing a microscope slide. The slides are removed from the test solution with forceps and laid horizontally to dry on a wide-mouth 4-ounce bottle. When dry, they are placed in the same 4-ounce bottle and 10 4- to 5-day-old mosquitoes of mixed sexes are added to each bottle. A piece of cotton gauze held on by an elastic band serves as a lid, and wad of cotton soaked in 10% honey solution serves as food. Mortality counts are made after 1 day at 80° F., 50% R.H. (relative humidity) Data obtained with the above procedures are reported in Table II below.

TABLE II

| | Control of Insects and Acarids - Percent Mortality | | | | | | | | | | | | | |
|---|---|---|---|---|---|---|---|---|---|---|---|---|---|---|
| | Tarnished plant Bug ppm. | Boll Weevil ppm. | Bean Aphid ppm. | | | Southern Armyworm ppm. | | Two-spotted Spider Mite ppm. | | Mexican Bean Beetle ppm. | | Western Potato Leafhopper ppm. | | Malaria Mosquito ppm. |
| Compound | 100 | 100 | 100 | 10 | 1 | 1000 | 100 | 300 | 100 | 100 | 10 | 100 | 10 | 10 |
| $(C_2H_5O)_2-\overset{S}{\underset{\parallel}{P}}-SCH_2-S-\overset{CH_3}{\underset{CH_3}{\overset{|}{C}}}-\langle\rangle$ | 94 | 95 | 100 | 100 | 85 | 100 | 100 | — | 75 | 100 | 40 | 100 | 100 | 100 |
| $(C_2H_5O)_2-\overset{S}{\underset{\parallel}{P}}-SCH_2-S-\overset{CH_3}{\underset{|}{CH}}-\langle\rangle$ | 70 | 0 | 100 | 100 | 100 | 100 | 30 | 100 | 0 | 100 | 0 | 100 | 100 | 100 |

TABLE II-continued

| | Control of Insects and Acarids - Percent Mortality | | | | | | | | | | | | |
|---|---|---|---|---|---|---|---|---|---|---|---|---|---|
| | Tarnished plant Bug ppm. | Boll Weevil ppm. | Bean Aphid ppm. | | Southern Armyworm ppm. | | Two-spotted Spider Mite ppm. | | Mexican Bean Beetle ppm. | | Western Potato Leafhopper ppm. | | Malaria Mosquito ppm. |
| Compound | 100 | 100 | 100 | 10 | 1 | 1000 | 100 | 300 | 100 | 100 | 10 | 100 | 10 | 10 |
| $(C_2H_5O)_2\text{-P(=S)-SCH}_2\text{-S(=O)-C(CH}_3)_2\text{-C}_6H_5$ | 0 | 100 | 100 | 100 | 100 | 100 | 80 | 100 | 100 | 100 | 40 | 100 | 100 | — |
| $(CH_3O)_2\text{-P(=S)-SCH}_2\text{-SC(CH}_3)_2\text{-C}_6H_4\text{-CN}$ | 0 | 90 | 100 | 100 | 100 | 100 | 100 | 100 | 100 | 90 | — | 100 | 100 | 60 |
| $(CH_3O)_2\text{-P(=S)-SCH}_2\text{-SC(CH}_3)_2\text{-C}_6H_3Cl_2$ (2,4) | 60 | 90 | 100 | 100 | 50 | 100 | 100 | 100 | 100 | — | — | 100 | 40 | 70 |
| $(C_2H_5O)_2\text{-P(=S)-SCH}_2\text{-SC(CH}_3)_2\text{-C}_6H_3Cl_2$ (2,4) | 0 | 50 | 100 | 100 | 50 | 100 | 100 | 100 | 90 | 0 | — | 100 | 50 | 30 |
| $(CH_3O)_2\text{-P(=S)-SCH}_2\text{-SC(CH}_3)_2\text{-C}_6H_3Cl_2$ (2,3) | 0 | 0 | — | — | 75 | 100 | 0 | 0 | 0 | 60 | — | 100 | — | 90 |
| $(CH_3O)_2\text{-P(=S)-SCH}_2\text{-S-C(CH}_3)_2\text{-C}_6H_5$ | 90 | 100 | 100 | 100 | 80 | 100 | 100 | 100 | 100 | 80 | 80 | 100 | 100 | — |
| $(C_2H_5O)_2\text{-P(=S)-SCH}_2\text{-S-C(CH}_3)(C_2H_5)\text{-C}_6H_5$ | 0 | 0 | 100 | 100 | 100 | 100 | 0 | 50 | 0 | 0 | — | 100 | 0 | 70 |
| $(C_2H_5O)_2\text{-P(=S)-SCH}_2\text{-S-C(C}_2H_5)_2\text{-C}_6H_5$ | 0 | 0 | 100 | 100 | 0 | 100 | 0 | 0 | — | 90 | 0 | 0 | — | 0 |
| $n\text{-C}_3H_7S,C_2H_5O\text{-P(=O)-SCH}_2S\text{-C(CH}_3)_2\text{-C}_6H_5$ | 0 | 0 | 100 | 100 | 90 | 100 | 100 | 100 | 100 | 80 | 80 | 100 | 0 | 0 |
| $(C_2H_5O)\text{-P(=S)-SCH}_2\text{-S-C(CH}_3)_2\text{-C}_6H_4\text{-CH}_3$ | 0 | — | 100 | 100 | 0 | 100 | 20 | 0 | — | — | — | 0 | — | 0 |
| $(C_2H_5O)_2\text{-P(=S)-SCH}_2\text{-S-C(CH}_3)_2\text{-C}_6H_4\text{-Cl}$ | 0 | 0 | 100 | 100 | 90 | 100 | 100 | 100 | 100 | 100 | 40 | 100 | 100 | 75 |
| $(CH_3O)_2\text{-P(=S)-SCH}_2\text{-S-C(CH}_3)_2\text{-C}_6H_4\text{-Br}$ | 40 | 100 | 100 | 100 | 100 | 100 | 100 | 100 | 100 | — | 0 | 100 | 0 | 75 |
| $(C_2H_5O)_2\text{-P(=S)-SCH}_2\text{-S-C(CH}_3)_2\text{-C}_6H_3Cl_2$ | 0 | 50 | 100 | 90 | 0 | 100 | 100 | 100 | 100 | 30 | 0 | 100 | 0 | 0 |
| $(CH_3O)_2\text{-P(=S)-SCH}_2\text{-S-C(CH}_3)_2\text{-C}_6H_3Cl_2$ | 40 | 70 | 100 | 100 | 98 | 100 | 100 | 100 | 100 | 30 | 0 | 100 | 0 | 67 |
| $(CH_3O)_2\text{-P(=S)-SCH}_2\text{-S-C(CH}_3)_2\text{-C}_6H_4\text{-Cl}$ | 0 | 100 | 100 | 100 | 100 | 100 | 100 | 100 | 100 | 50 | 0 | 100 | 0 | 100 |

TABLE II-continued

| Compound | Control of Insects and Acarids - Percent Mortality | | | | | | | | | | | | |
|---|---|---|---|---|---|---|---|---|---|---|---|---|
| | Tarnished plant Bug ppm. | Boll Weevil ppm. | Bean Aphid ppm. | | Southern Armyworm ppm. | | Two-spotted Spider Mite ppm. | | Mexican Bean Beetle ppm. | | Western Potato Leafhopper ppm. | Malaria Mosquito ppm. |
| | 100 | 100 | 100 | 10 | 1 | 1000 | 100 | 300 | 100 | 100 | 10 | 100 10 | 10 |
| $CH_3O\underset{P}{\overset{O}{\|}}SCH_2-S-\underset{CH_3}{\overset{CH_3}{C}}-\langle\rangle-Cl$ / $CH_3S$ | 0 | 90 | 100 | 100 | 95 | 100 | 0 | 50 | 0 | 40 0 | | 100 0 | 0 |

EXAMPLE 36

Mammalian Toxicity Studies ($LD_{50}$ for Rats and Mice)

Twenty male albino rats or mice of the Carworth Farms Nelson strain (CFI strain for mice)(or other suitable strain) weighing approximately 90 to 120 grams (18-20g. for mice) are selected. Basically, these animals are fasted 24 hours before dosing. Mice are not fasted.

For materials which are soluble or easily dispersed in an aqueous medium, a 20% solution or suspension is prepared in an aqueous solution of 0.2% agar and 0.1% "Tween" 80. The same series of dosages (grams or milliliters of material per kilogram of animal body weight) are used for all materials in this test. If no previous information is available on the compound or its analogs, a miximum dosage of 10 g/kg is selected to differ by a geometric factor of 2 from the preceding dose, i.e., 10, 5, 2.5, 1.25 g/kg. A sufficient number of dosages are given so as to bracket a 50% response. The animals are observed for several hours after dosing and daily over a 14-day observation period. At the end of this period the survivors are sacrificed, weighed and subjected to a gross autopsy. The results are tabulated and the $LD_{50}$ is calculated by the method of moving averages using the tables constructed by Weil. [Weil, C. S., Biometrics, 8: (3), 249-263, 1952].

Samples received as liquids may be administered undiluted or as suspensions in aqueous Agar-Tween, depending on the viscosity of the material. If the material is believed to be relatively non-toxic, an initial maximum dosage of 10 ml/kg is selected and subsequent dosages are selected based upon the severity of gross signs of toxicity.

For organic phosphate anticholinesterase insecticides, the procedure is modified somewhat. The phosphates are readied for administration by preparing a solution or dispersion in corn oil (Mazola), the concentration of which is adjusted so that the total volume of the dose is 20 ml/kg (0.5 ml/kg in mouse) in every case. The initial solution is prepared by deciding upon the maximum dosage in mg/kg to be administered and preparing 50 ml. (10 in mouse test) of this solution of such a concentration that the desired dosage in mg/kg is delivered when 2 ml. (0.5 ml. in mouse test) of the solution is administered for 100 g (20 g in mouse) of rat body weight. Serial dilutions differing by a factor of two are then prepared for each lower dosage level.

$LD_{50}$ values obtained by the above procedures are reported in the Table III below where it can be seen that compounds having the structure where $R_3$ and $R_4$ are methyl are generally much less toxic to mammals than derivatives in which $R_3$ and $R_4$ are hydrogen. Moreover, when these data are coupled with the insecticidal and acaricidal activity of the test compounds, it can also be seen that compounds having the structure where $R_3$ and $R_4$ are alkyl, and at least one of X, Y and Z is a substitutent other than hydrogen, are preferred.

TABLE III $LD_{50}$ Values For Test Compounds $$R_1\underset{R_2O}{\overset{A}{\underset{\|}{P}}}-SCH_2-S(O)_n-\underset{R_4}{\overset{R_3}{C}}-\langle X,Y,Z\rangle$$

| Structure | | | | | | | | | LD$_{50}$ | |
|---|---|---|---|---|---|---|---|---|---|---|
| | | | | | | | | | Mice | Rats |
| $(C_2H_5O)_2\overset{S}{\underset{\|}{P}}-SCH_2-S-C_2H_5$ | | | | | | | | | 5.6 | 1-5 |
| $(C_2H_5O)_2\overset{S}{\underset{\|}{P}}-SCH_2-SCH_2-\langle\rangle$ | | | | | | | | | 67 | 25* |

| $R_1$ | $R_2$ | n | $R_3$ | $R_4$ | A | X | Y | Z | | |
|---|---|---|---|---|---|---|---|---|---|---|
| $C_2H_5O$ | $C_2H_5$ | 0 | $CH_3$ | $CH_3$ | S | H | H | H | 71 | 18 |
| $C_2H_5O$ | $C_2H_5$ | 0 | $CH_3$ | H | S | H | H | H | 67 | — |
| $C_2H_5O$ | $C_2H_5$ | 1 | $CH_3$ | $CH_3$ | S | H | H | H | 88 | — |
| $CH_3O$ | $CH_3$ | 0 | $CH_3$ | $CH_3$ | S | H | H | H | 117 | 28 |
| $nC_3H_7S$ | $C_2H_5$ | 0 | $CH_3$ | $CH_3$ | O | H | H | H | — | 34 |
| $C_2H_5O$ | $C_2H_5$ | 0 | $CH_3$ | $CH_3$ | S | H | 4 Cl | H | — | 79 |
| $CH_3O$ | $CH_3$ | 0 | $CH_3$ | $CH_3$ | S | 3 Cl | 4 Cl | H | — | >200 |
| $CH_3O$ | $CH_3$ | 0 | $CH_3$ | $CH_3$ | S | H | 4 Cl | H | — | 230 |
| $C_2H_5O$ | $C_2H_5$ | 0 | $CH_3$ | $CH_3$ | S | 3 Cl | 4 Cl | H | — | 100 |

TABLE III-continued

LD₅₀ Values For Test Compounds $$\underset{R_2O}{\overset{R_1}{>}}\overset{A}{\underset{\|}{P}}-SCH_2-S(O)_n-\underset{R_4}{\overset{R_3}{\underset{|}{C}}}-\underset{Z}{\overset{X,Y}{\bigcirc}}$$

| Structure | LD₅₀ Mice | LD₅₀ Rats |
|---|---|---|
| $(C_2H_5O)_2\overset{S}{\underset{\|}{P}}-SCH_2-S-C_2H_5$ | 5.6 | 1–5 |
| $(C_2H_5O)_2\overset{S}{\underset{\|}{P}}-SCH_2-SCH_2-\bigcirc$ | 67 | 25* |

| R₁ | R₂ | n | R₃ | R₄ | A | X | Y | Z | — | — |
|---|---|---|---|---|---|---|---|---|---|---|
| CH₃O | CH₃ | 0 | CH₃ | CH₃ | S | H | 4Br | H | — | 280 |
| CH₃O | CH₃ | 0 | CH₃ | CH₃ | S | 2Cl | H | 5Cl | — | 800 |
| CH₃O | CH₃ | 0 | CH₃ | CH₃ | S | H | 2Cl | 3Cl | — | >500 |

*Value reported in the literature.

EXAMPLE 37

Cut-Stem Systemic Test (Sourthern Armyworm)

The compound to be tested is formulated as an emulsion containing 0.1 gram of test material, 0.2 gram of Alrodyne 315 emulsifier, 10 ml. of acetone and 90 ml. of water. This is diluted tenfold with water to give a 100 ppm. emulsion for the initial test. A sieva lima bean plant with only the primary leaves unfolded is cut off just above soil level and inserted into a 2-ounce bottle of 100 ppm. emulsion and held in place by a bit of cotton wrapped around the stem. The bottle is then placed in a ventilated box with the leaves extending outside the box, such that any possible fumes from the compound will be drawn out the end of the box rather than rising to affect the test leaves. After holding 3 days at 80° F. and 60% R.H., one leaf from each plant is placed on a moist filter paper in the bottom of a petri dish. Ten third-instar Southern armyworm larvae are then added to each dish and mortality counts made after holding another 3 days at 80° F. and 60% R.H.

Mites

The same procedure described above is employed in the mite systemic evaluation excepting that the sieva lima bean leaves are infested with mites, both adult and nymphs, while the leaves are in the ventilated box. After 3 days the leaves are removed and examined under a microscope to determine percent mortality. Data obtained are reported in the Table IV below where it can be seen that the compounds of the present invention are systemically effective insecticidal agents.

TABLE IV

STRUCTURE: $\underset{R_2O}{\overset{R_1}{>}}\overset{A}{\underset{\|}{P}}-SCH_2S(O)_n-\underset{R_4}{\overset{R_3}{\underset{|}{C}}}-\underset{Z}{\overset{X,Y}{\bigcirc}}$ Systemic Insecticidal Activity — % Mortality

| R₁ | R₂ | A | N | R₃ | R₄ | X | Y | Z | Mites | Southern Armyworms |
|---|---|---|---|---|---|---|---|---|---|---|
| C₂H₅O | C₂H₅ | S | 0 | CH₃ | CH₃ | H | H | H | 80 | 100 |
| n-C₃H₇S | C₂H₅ | O | 0 | CH₃ | CH₃ | H | H | H | 90 | 0 |
| C₂H₅O | C₂H₅ | S | 0 | CH₃ | CH₃ | 3-Cl | 4-Cl | H | 100 | 100 |
| CH₃O | CH₃ | S | 0 | CH₃ | CH₃ | H | 4-Br | H | 100 | 100 |
| CH₃O | CH₃ | S | 0 | CH₃ | CH₃ | H | 4-Cl | H | 100 | 100 |
| CH₃S | CH₃ | O | 0 | CH₃ | CH₃ | H | 4-Cl | H | 30 | 0 |
| CH₃O | CH₃ | S | 0 | CH₃ | CH₃ | H | 3-Cl | 4-Cl | 30 | 90 |

We claim:

1. A method for the control of insects and acarids comprising applying to the habitat of said insects and acarids an insecticidally or acaricidally effective amount of the compound having the formula:

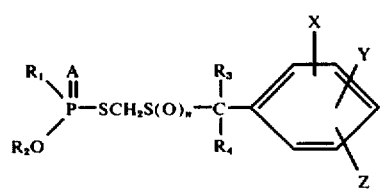

wherein R₁ represents a member selected from the group consisting of $C_1$-$C_4$ alkyl, $C_1$-$C_4$ alkoxy, $C_3$-$C_6$ alkoxyalkyl, $C_3$-$C_6$ alkoxyalkylthio and $C_1$-$C_4$ alkylthio; R₂ is $C_1$-$C_4$ alkyl; R₃ represents a member selected from the group consisting of hydrogen and $C_1$-$C_4$ alkyl; R₄ is $C_1$-$C_4$ alkyl; A represents a member selected from the group consisting of sulfur and oxygen; $n$ represents an integer selected from 0, 1 and 2; X and Y each represent members selected from the group consisting of hydrogen, alkyl $C_1$-$C_4$ and halogen; and Z represents a member selected from the group consisting of hydrogen, $C_1$-$C_4$ alkyl, $C_1$-$C_4$ alkoxy, cyano, halogen, $C_1$-$C_4$ alkylthio, $CCl_3$, $CF_3$ and nitro.

2. A method according to claim 1 wherein the habitat is the foliage of plants or the soil in which they are grown, comprising applying to the foliage of said plants or the soil in which they are grown, an insecticidally or acaricidally effective amount of a compound of claim 1.

3. A method according to claim 1, wherein the compound is O,O-dimethyl S-(3,4-dichloro-α, α-dimethylbenzylthio)-methyl phosphorodithioate.

4. A method according to claim 1, wherein the compound is O,O-dimethyl S-(p-chloro-α, α-dimethylbenzylthio)methyl phosphorodithioate.

5. A method according to claim 1, werein the compound is S-(p-chloro-α, α-dimethylbenzylthio)methyl O,O-diethyl phosphorodithioate.

6. A method according to claim 1, wherein the compound is S-(p-chloro-α, α-dimethylbenzylthio)methyl O-methyl S-methyl phosphorodithioate.

7. A method according to claim 1, wherein the compound is S-(α, α-dimethylbenzylthio)methyl O,O-diethyl phosphorodithioate.

8. A method according to claim 1, wherein the compound is S-(3,4-dichloro-α, α-dimethylbenzylthio)-methyl O,O-diethyl phosphorodithioate.

9. A method according to claim 1, wherein the compound is S-(p-bromo-α, α-dimethylbenzylthio)methyl O,O-dimethyl phosphorodithioate.

10. A method according to claim 1, wherein the compound is S-(α, α-dimethylbenzylthio)methyl O,O-dimethyl phosphorodithioate.

* * * * *